United States Patent
Guerret

(10) Patent No.: US 7,893,163 B2
(45) Date of Patent: Feb. 22, 2011

(54) GRADIENT COPOLYMERS SOLUBLE OR AT LEAST DISPERSIBLE IN WATER AS WELL AS IN ORGANIC SOLVENTS

(75) Inventor: Olivier Guerret, Mazerolles (FR)

(73) Assignee: Arkema France, Colombes (FR)

( * ) Notice: Subject to any disclaimer, the term of this patent is extended or adjusted under 35 U.S.C. 154(b) by 428 days.

(21) Appl. No.: 10/538,730

(22) PCT Filed: Dec. 11, 2003

(86) PCT No.: PCT/FR03/03669

§ 371 (c)(1), (2), (4) Date: Jun. 13, 2005

(87) PCT Pub. No.: WO2004/055071

PCT Pub. Date: Jul. 1, 2004

(65) Prior Publication Data

US 2006/0058467 A1 Mar. 16, 2006

(30) Foreign Application Priority Data

Dec. 13, 2002 (FR) .................................. 02/15852

(51) Int. Cl.
  C08F 253/00 (2006.01)
  C08F 20/06 (2006.01)
  C08F 20/68 (2006.01)
  C08F 118/02 (2006.01)
  C08L 31/00 (2006.01)

(52) U.S. Cl. .................... 525/259; 525/262; 526/317.1; 526/318; 526/319; 524/556

(58) Field of Classification Search ................. 525/262, 525/259; 524/556; 526/318, 319, 317.1
See application file for complete search history.

(56) References Cited

U.S. PATENT DOCUMENTS

| | | | |
|---|---|---|---|
| 5,807,937 A * | 9/1998 | Matyjaszewski et al. | 526/135 |
| 6,153,705 A | 11/2000 | Corpart et al. | |
| 6,262,206 B1 * | 7/2001 | Nesvadba et al. | 526/220 |
| 6,437,040 B2 | 8/2002 | Anthony et al. | |
| 6,642,318 B1 | 11/2003 | Chiefari et al. | |
| 6,747,111 B2 | 6/2004 | Chiefari et al. | |
| 6,812,291 B1 | 11/2004 | Corpart et al. | |
| 2001/0008928 A1 | 7/2001 | Nesvadba et al. | |
| 2001/0039315 A1 | 11/2001 | Nesvadba et al. | |
| 2002/0198347 A1 | 12/2002 | Adam et al. | |
| 2004/0171777 A1 | 9/2004 | Le et al. | |

OTHER PUBLICATIONS

Matyjaszewski et al. "Gradient copolymers by atom transfer radical polymerization", J. Phys. Org. Chem., 2000, 13, p. 775-786.*
Farcet et al. "Nitroxide-mediated miniemulsion polymerization of n-butyl acrylate: synthesis of controlled homopolymers and gradient copolymers with styrene", Macromolecular Symposia (2002), 182, (3rd IUPAC-Sponsored International Symposium on Free-Radical Polymerization: Kinetics and Mechanism), 2001, 249-260 (see SRNT dated on Sep. 19, 2007.*

* cited by examiner

*Primary Examiner*—Michael M Bernshteyn
(74) *Attorney, Agent, or Firm*—Thomas F. Roland

(57) ABSTRACT

The invention concerns amphiphilic copolymers, in particular gradient amphiphilic copolymers obtained by controlled free radical solution or mass polymerization. The invention also concerns a method for aqueous dissolution of said copolymers. The inventive copolymers are useful in surface treatment techniques and can be used in formulations for paints, adhesives, glues as well as in cosmetics.

14 Claims, 1 Drawing Sheet

Incorporation of the STY,MAA mixture as a function
of the conversion (level of starting acrylate: 80%)

GRADIENT COPOLYMERS SOLUBLE OR AT LEAST DISPERSIBLE IN WATER AS WELL AS IN ORGANIC SOLVENTS

This application claims benefit, under U.S.C. §119 or §365 of French Application Number 02/15852, filed Dec. 13, 2002; and PCT/FR2003/003669 filed Dec. 11, 2003.

FIELD OF THE INVENTION

The invention relates to the field of amphiphilic copolymers, particularly to the field of amphiphilic gradient copolymers and more particularly to the field of gradient copolymers which are soluble or dispersible in water as well as in organic solvents.

It also relates to a process for the synthesis of these gradient copolymers and to a process for employing such polymers in solution in water or in a water/alcohol mixture at concentrations of greater than or equal to 5%.

The invention also relates to the use of such solutions in formulations which can be used in different sectors of application, such as cosmetics, aqueous paints, adhesion to surfaces having little natural affinity for water, or the dispersion of inorganic fillers.

BACKGROUND OF THE INVENTION

Generally, a polymer material may be described by the following three quantities: number-average mass, denoted below by Mn; weight-average mass, denoted below by Mw; and the polydispersity index PI.

These three quantities are sufficient to describe a homopolymer or a copolymer, provided that its chemical composition is well known. In fact, the following definitions will demonstrate that a gradient copolymer has to be described much more specifically and that the parameters of its synthesis will be determining in order to describe it correctly.

In what follows, the abbreviation Tg denotes the glass transition temperature of a polymer.

In the present invention, the term "hydrophilic monomer" will denote, without distinction, monomers having corresponding homopolymers which are soluble in water or dispersible in water or having an ionic form which is soluble in water or dispersible in water.

A homopolymer is said to be soluble in water if it forms a clear solution when it is in solution at 5% by weight in water at 25° C.

A homopolymer is said to be dispersible in water if, at 5% by weight in water at 25° C., it forms a stable suspension of fine, generally spherical, particles. The mean size of the particles constituting said dispersion is less than 1 µm and more generally varies between 5 and 400 nm, preferably from 10 to 250 nm. These particle sizes are measured by light scattering.

The following definitions are of use in making it possible to distinguish gradient copolymers from other copolymers and polymers:

Controlled Radical Polymerization:
  Radical polymerization controlled by nitroxides. WO 96/24620 or WO 00/71501 discloses the devices of this polymerization and their use. The scientific understanding of such a control technique is described by Fischer in Chemical Reviews, 2001, 101, 3581, by Tordo and Gnanou in J. Am. Chem. Soc., 2000, 122, 5929, and Hawker in J. Am. Chem. Soc., 1999, 121, 3904, for example.
  Atom transfer radical polymerization. Disclosed in WO 96/30421, it proceeds by reversible insertion with regard to an organometallic complex in a bond of carbon-halogen type.
  Radical polymerization controlled by sulfur derivatives of xanthate, dithioester, trithiocarbonate or trithiocarbamate type. Reference may be made to the following documents: FR 01/02848, WO 02/068550, WO 98/01478, WO 99/35177, WO 98/58974, WO 99/31144 or WO 97/01478, a reference publication in the field being: Rizzardo et al., Macromolecules, 1998, 31, 5559.

Controlled radical polymerization denotes polymerizations for which the side reactions which usually result in the disappearance of the propagating entities (termination or transfer reaction) are rendered highly improbable with respect to the propagation reaction by virtue of an agent for controlling the free radicals. The shortcoming of this method of polymerization lies in the fact that, when the concentrations of free radicals become high with respect to the concentration of monomer, the side reactions again become determining and tend to broaden the distribution of the masses.

Gradient

Gradient copolymer: the gradient copolymer is a copolymer of at least two monomers generally obtained by living or pseudoliving polymerization. By virtue of these methods of polymerization, the polymer chains grow simultaneously and thus incorporate, at each instant, the same ratios of comonomers. The distribution of the comonomers in the polymer chains thus depends on the change, during the synthesis, in the relative concentrations of the comonomers. Reference will be made to the following publications for a theoretical description of gradient copolymers: T. Pakula et al., Macromol. Theory Simul., 5, 987-1006 (1996); A. Aksimetiev et al., J. of Chem. Physics, 111, No. 5; M. Janco, J. Polym. Sci., Part A: Polym. Chem. (2000), 38(15), 2767-2778; M. Zaremski et al., Macromolecules (2000), 33(12), 4365-4372; K. Matyjaszewski et al., J. Phys. Org. Chem. (2000), 13(12), 775-786; Gray Polym. Prepr. (Am. Chem. Soc., Div. Polym. Chem.) (2001), 42(2), 337-338; K. Matyjaszewski, Chem. Rev. (Washington, D.C.) (2001), 101(9), 2921-2990.

Natural gradient: will be used for a gradient copolymer synthesized under batchwise conditions from a starting mixture of comonomers. The distribution of the various monomers in the chain thus follows a law deduced from the relative reactivity and from the starting concentrations of monomers. These polymers constitute the simplest class of gradient copolymers as it is the starting mixture which defines the final product property.

Artificial gradient: will be used for a copolymer, the concentration of monomers of which will be varied during the synthesis by a processing stratagem.

Composition gradient: this is the G function defined by $$\vec{G}(x) = \sum \overline{[M_i](x)}$$

where x denotes the standardized position on the polymer chain and $[M_i](x)$ denotes the relative concentration in this position of the monomer $M_i$ (expressed in moles). In the case of isoreactive monomers, $[M_i](x)=\frac{1}{2}$.

The G(x) function thus describes the composition of the gradient polymer locally. Two copolymers can have an equivalent overall composition but very different G(x) functions. The factors determining the G(x) functions are the relative reactivity coefficients of the monomers ($r_i$ for the monomer $M_i$) (which depend mainly on the type of process of synthesis (homogeneous, disperse) and on the solvents, and the like), the starting concentrations of the monomers and the additions of monomers during the polymerization. Mention may be made, by way of example, of the textbook case of a gradient copolymer of styrene ($M_1$) and of methacrylic acid ($M_2$) in a homogeneous polymerization system. The literature gives us r1=0.418 and r2=0.6.

The variation in the starting concentrations of styrene and of methacrylic acid makes it possible to obtain different gradient copolymers thus having chains with completely different structures. Thus, at 10% of methacrylic acid, a very low gradient copolymer is obtained for which nanostructuring cannot be expected, at 20% a copolymer with a hydrophilic "head" and a hydrophobic tail is obtained with a sufficiently pronounced gradient to result in nanostructuring. On the other hand, at 50%, the monomers being isoreactive under these conditions, the copolymer obtained is of the alternating type.

Despite the fact that each of the polymers described is a gradient polymer of styrene and of methacrylic acid, the difference in starting concentration of the monomers results in chains with completely different structures, conferring different properties on the copolymers.

This example thus illustrates the importance of the starting monomer concentrations on the arrangement of the different monomers along the chain.

Block Copolymer:

This is in fact a subclass of the family of the artificial gradient copolymers. $[M_i](x)$ is then the product of at least one Dirac function by a monotone function, which reflects the fact that the mixture of monomers changes from one form to another in the chain due to a change undergone by the monomers in the reaction medium (stripping of the first mixture or addition of at least one new monomer). Some block copolymers are distinguished in that they have a random hinge between the two blocks.

In WO 02/068550, the authors disclose and claim block polymers of $(AB)_n$-core type (with n greater than or equal to 2) with optionally a hinge between the A and B blocks; such structures correspond to the following GA(x) curves, as shown in FIG. 1:

It is therefore seen that the structure of such a chain is:
  symmetrical
  the notion of block is reflected by a zone at least of the chain where the composition of A is 1 and of B is 0,
  such structures correspond to a process of synthesis based on the polymerization of a first mixture of monomers and then of a second with optionally purification between the two stages of the polymer to avoid the hinge block.

Such compounds are nanostructures and therefore exhibit physical and rheological properties in keeping with this nanostructuring: the order/disorder temperature is high. Up to this temperature, the viscosity of the polymer is very high and one of the consequences is that it is difficult, indeed even impossible, to dissolve such polymers in aqueous solution or in a solvent.

It emerges from these definitions and from these examples that the G(x) functions, the number-average mass and the polydispersity index are three necessary and sufficient pieces of information which differentiate one gradient copolymer from another. It also emerges that the G(x) function is directly determined by the process of synthesis.

Surprisingly, the Applicant Company has discovered that amphiphilic gradient polymers having at least one hydrophilic monomer and at least one monomer $M_1$, the homopolymer of which corresponding to a $Tg_1$ of less than 20° C., exhibit the advantage of being easy to handle in water or in a solvent in comparison with block copolymers while retaining rheological properties which are advantageous for applications such as paint, varnishes, adhesion, filler dispersion or even formulations for medical, dermatological or cosmetic use, it being possible for the monomer $M_1$ to be a hydrophilic monomer.

DETAILED DESCRIPTION OF THE INVENTION

Figure 1:
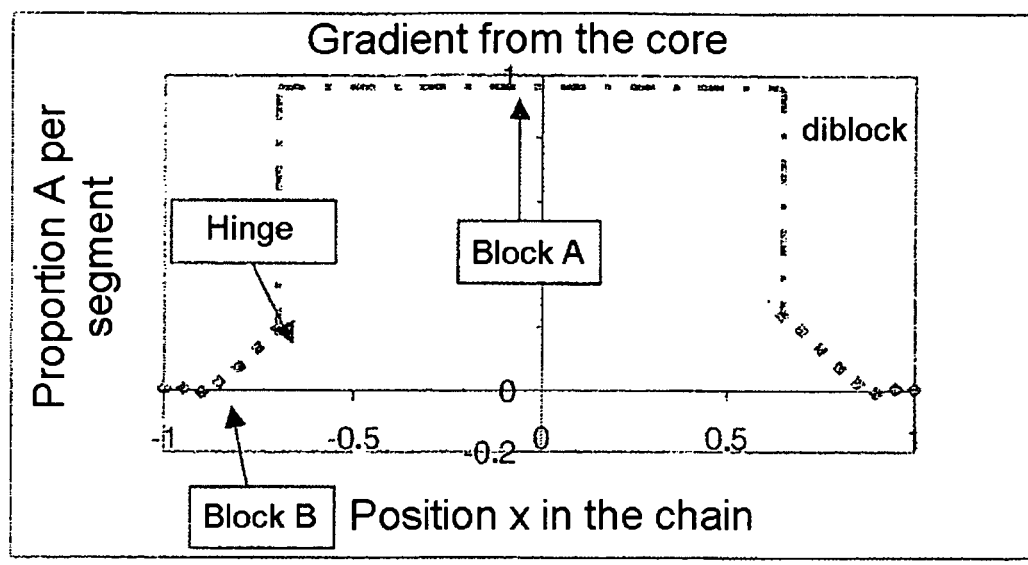
FIG. 1 represents a GA(x) curve for block copolymers with an optional hinge between the A and B blocks.

The first subject matter of the invention is a gradient copolymer comprising at least two monomers, the first ($M_1$), the homopolymer of which corresponding to a $Tg_1$ of less than 20° C., represents at least 50% by weight of the total weight of the copolymer, the second ($M_2$), the homopolymer of which corresponding to a $Tg_2$ of greater than 20° C. and preferably of greater than 50° C., represents at most 50% by weight of the total weight of the copolymer. Furthermore, at least one of the monomers must be hydrophilic and represent at least 5% by weight of the total weight of the copolymer.

The copolymer of the invention comprises at least one monomer $M_i$ such that the probability of encountering $M_i$ in any standardized position x situated along the polymer chain is nonzero.

Preferably, $Tg_1$ is between −150° C. and 20° C. and more preferably between −120° C. and 15° C.

According to a preferred form of the invention, the hydrophilic monomer represents at least 10% by weight of the weight of the copolymer.

In addition, the gradient copolymer of the invention exhibits average masses of between 5000 g/mol and 1 000 000 g/mol and exhibits polydispersity indices of between 1.1 and 2.5, preferably between 1.1 and 2.

The hydrophilic monomers can be chosen from the following monomers, which are spontaneously hydrophilic or which are rendered hydrophilic by simple transformation (quaternization of an amine or neutralization of an acid) in the polymer structure:
  ethylenic carboxylic acids, such as acrylic acid, methacrylic acid, itaconic acid or fumaric acid,
  acrylates and methacrylates of polyethylene glycol or of glycol which are or are not substituted on their end functional group by alkyl, phosphate, phosphonate or sulfonate groups,
  amides of unsaturated carboxylic acids, such as acrylamide or methacrylamide and their N-substituted derivatives,
  aminoalkyl acrylates and methacrylates, and aminoalkylmethacrylamides,
  carboxylic anhydrides carrying a vinyl bond, such as maleic anhydride or fumaric anhydride,
  vinylamides, such as vinylpyrrolidone or vinylacetamide,
  vinylamines, such as vinylmorpholine or vinylamine,
  vinylpyridine.

Preferably, $M_1$ is chosen from the following monomers:
  linear or branched $C_1$-$C_{12}$ alkyl acrylates,
  polyethylene glycol (meth)acrylates,
  dienes, such as butadiene or isoprene.

The other monomers ($M_2$) participating in the copolymer of the invention are chosen from the following monomers:
  styrene derivatives,
  (meth)acrylic derivatives resulting in polymers with high Tg values, such as norbornyl acrylate or methyl methacrylate,
  acrylonitrile and methacrylonitrile.

The gradient copolymers of the invention can be obtained by controlled radical polymerization, in particular according to the procedure described below:

1) The mixture of the monomers to be polymerized, a radical polymerization initiator and an agent for controlling the polymerization are introduced into a stirred reactor which may or may not contain a solvent. The mixture is placed under an atmosphere of a gas which is inert with respect to radical polymerization, such as nitrogen or argon. Alkyl acetates, such as, inter alia, butyl acetate or ethyl acetate, aromatic solvents, ketone solvents or alcoholic solvents will advantageously be chosen as optional polymerization solvent. In the case where the mixture of monomers is miscible with water, the latter can advantageously be used as solvent.

2) The mixture is brought with stirring to the desired polymerization temperature. This temperature is chosen within a range from 10° C. to 160° C., preferably from 25° C. to 130° C. The choice of the polymerization temperature should be optimized according to the chemical composition of the mixture of monomers. Specifically, certain monomers having very high kinetic propagation constants and a lower affinity for the control agent must be polymerized at low temperature (for example, in the case of a significant proportion of methacrylic derivatives, polymerization at a temperature of between 25° C. and 80° C. will be preferred).

3) The polymerization medium is optionally modified during the polymerization (before achieving 90% conversion of the starting monomers) by supplementary addition of one or more of the monomers of the starting mixture. This addition can be carried out in different ways, ranging from sudden addition to continuous addition over the complete duration of the polymerization.

4) The polymerization is halted when the desired conversion is achieved. The overall composition of the polymer and the G(x) function depend on this conversion. Preferably, more than 50% conversion will be achieved. The achievement of more than 90% conversion is also preferred.

5) The possible residual monomers are removed, either by evaporation or by addition of an amount of conventional polymerization initiator, such as peroxide or azo derivatives.

According to the invention, the agent for controlling the polymerization is the nitroxide (I). The process according to the invention consists of the synthesis of the copolymers in the presence of nitroxides (I):

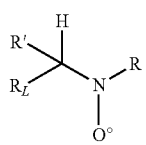

(I)

where R' and R, which are identical or different and which are optionally connected so as to form a ring, are alkyl groups having between 1 and 40 carbon atoms which are optionally substituted by hydroxyl, alkoxy or amino groups. In particular, R and R' will be tert-butyl groups.

and where $R_L$ is a monovalent group with a molar mass of greater than 16 g/mol which can be a phosphorus or aromatic group; in particular, $R_L$ is a phosphorus group and more particularly a phosphonate group of formula:

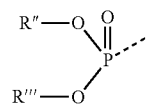

where R" and R''', which are identical or different and which are optionally connected so as to form a ring, are alkyl groups having between 1 and 40 carbon atoms which are optionally substituted by hydroxyl, alkoxy or amino groups. In particular, R" and R''' will be ethyl groups.

Conventional (azo or peroxide) polymerization initiators can be used while observing a nitroxide/initiator molar ratio of between 2 and 2.5, if it is considered that one mol of these initiators gives rise to two mol of polymer chains, or between 1 and 1.25 for monofunctional initiators.

Alkoxyamines of general formula (II) can advantageously be chosen to initiate the polymerization and to release, at the same time, the nitroxide which controls this polymerization,

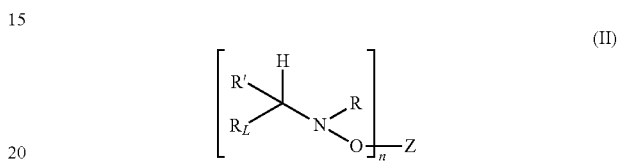

(II)

where n is a integer of less than or equal to 8 and preferably of between 1 and 3 and Z is a monovalent or multivalent radical of styryl, acryloyl or methacryloyl type, the other radicals having the same meanings as above. The quality of the control of the polymerization can be improved by adding nitroxide (I) to the alkoxyamine (II) in a proportion ranging from 0 to 20 mol % with respect to the moles of alkoxyamine functional groups (one mol of polyvalent alkoxyamine contributes a number of alkoxyamine functional groups proportional to its valency).

The choice of the initiator will be dictated by the requirements of the application:
- a monofunctional initiator will result in asymmetric chains,
- a polyfunctional initiator will result in macromolecules having a symmetry starting from a core.

The choice of the hydrophilic/hydrophobic monomers will be dictated by the importance of situating the hydrophilic monomers at a precise point on the chain.

Thus, if it is desired for the hydrophilic units to be in the core of a polymer chain, a difunctional initiator and a mixture of monomers such that the reactivity of the hydrophilic monomers is greater than that of the hydrophobic monomers will be chosen; this is the case, for example, with methacrylic acid with respect to acrylate monomers in general. In the case where the hydrophilic units are desired at the periphery, the contrary case will be chosen, such as, for example, the acrylate/vinylpyrrolidone pair.

The copolymers of the invention are water-soluble or water-dispersible. They are of use in formulations for paints, adhesives, glues and cosmetics. They are also of use for pigment dispersion.

One of the other subject matters of the invention is a process for the aqueous dissolution of the gradient copolymers of the invention which comprises:

1) Dissolving the polymer in a ketone solution at a level of solid of between 20 and 90%, preferably between 20 and 50%; preferably, acetone or methyl ethyl ketone (MEK) will be chosen.

2) In the case of hydrophilic monomers of acid type, an at least one 1M solution of base, such as a salt of hydroxonium ion (OH$^-$), an amine, ammonia, a carbonate (CO$_3^{2-}$) salt or a hydrogencarbonate (HCO$_3^-$) salt, is added to the vigorously stirred solution. In the case of hydrophilic monomers of amine type, an at least 1M solution of acid, such as hydrochloric acid, hydrobromic acid, hydriodic acid, acetic acid, propionic acid, sulfuric acid, phosphoric acid or hydroboric acid, is added. In the case of neutral hydrophilic monomers, such as dimethylacrylamide or vinylpyrrolidone, the solution obtained in 1 is left unchanged.

3) Water is then added, with vigorous stirring, to the solution obtained in 1 or optionally in 2 in a proportion such that the level of solid obtained is between 1 and 80%. Optionally, the water can be replaced by water/alcohol mixtures in proportions ranging from 99/1 to 50/50.

4) The ketone is evaporated by conventional evaporation techniques, in particular by stirring the solution at 100° C. Concentrating is continued until the desired level of solid is obtained.

This is because the Applicant Company has noticed that, in order to succeed in the aqueous dissolution of such polymers, it was advisable for the latter to be first dissolved in an organic solution.

Another subject matter of the present invention relates to the use of such polymers in solution in water or in a water/alcohol mixture at concentrations greater than or equal to 5%. The aqueous or organic solutions of such polymers also form part of the invention.

The invention also relates to the use of such solutions in formulations which can be used in various sectors, such as cosmetics, paints, adhesion to surfaces having little natural affinity for water, or the dispersion of inorganic fillers.

EXAMPLES

The following examples illustrate the invention without limiting the scope thereof.

Characterization of the Polymers:

The molar masses and their distribution were determined by steric exclusion chromatography (SEC) by universal calibration using polystyrenes as standard and the Mark-Houwink coefficients of PMMA for the copolymers.

The chemical composition of the copolymers can be determined by proton NMR, UV spectrometry or infrared spectrometry.

The experimental characterization of the gradient is provided by the measurement during polymerization of the chemical composition of the polymer.

This is because, for the polymers prepared by living or pseudoliving polymerization, the length of the chains is linearly related to the conversion. In other words, if it is known what proportion of a monomer $M_1$ is incorporated at a given moment of the polymerization, the length which the chains will have at this moment of the polymerization will be known and thus the function $[M_2](x)$, where x is the position with respect to the total length of the chain, can be determined.

By withdrawing samples at different instants of the polymerization and by determining the difference in content of each monomer, the gradient is thus established.

Another method for determining the gradient function is the measurement, as the monomers are converted, of the Tg of the polymer. This is because, to a first approximation, the Tg can be estimated by the relationship:

$$\frac{1}{Tg} = \sum \frac{xi}{Tgi},$$

where $Tgi$ denotes the Tg of the homopolymer of the monomer i and $xi$ its mass fraction.

These methods reflect the average chemical composition of the material obtained by polymerization. In addition, it is important to demonstrate that all the chains of polymers have an analogous composition. For this, use will advantageously be made of liquid absorption chromatography, which makes it possible to separate the polymer chains no longer according to their molecular weight but according to their polarity. The latter reflects the chemical composition of the polymers constituting the material.

Initiators and Control Agent Used:

The stable free radical used as polymerization control agent in the examples and referenced SG1 corresponds to the following formula:

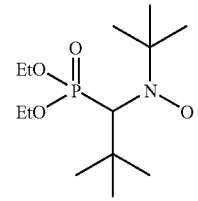

The alkoxyamines DIAMS and MONAMS mentioned in the examples correspond to the following formulae:

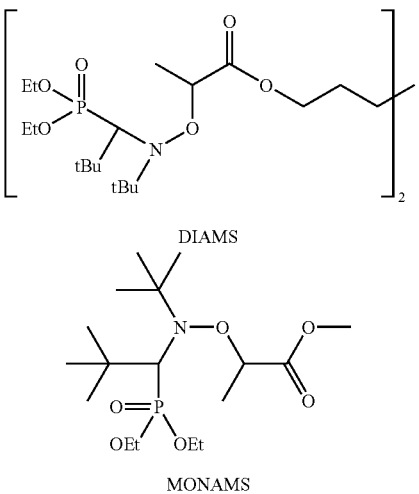

DIAMS

MONAMS

Relative Reactivity Coefficients of Some Monomers Used:

Some of the relative reactivity coefficients used in the examples are given in table 1:

TABLE 1

Reactivity coefficients r1, r2 of the pairs of monomers M1/M2

| M1 | M2 | | | | | | |
|---|---|---|---|---|---|---|---|
| | EA | S | MMA | MAA | AA | Maleic anhydride | NVP |
| EA | 1 | 0.18 | 0.11 | 0.31 | 0.91 | / | |
| S | 0.84 | 1 | 0.478 | 0.418 | 0.25 | 0.01 | 17 |
| MMA | 2.8 | 0.585 | 1 | | 1.28 | / | 5.2 |
| MAA | 1.25 | 0.6 | 0.48 | 1 | / | / | |
| AA | 1.31 | 0.136 | / | / | 1 | | / |
| Maleic anhydride | | 0.02 | 0.02 | / | / | | |
| NVP | | 0.05 | | | | | |

NVP N-Vinylpyrrolidone
EA Ethyl acrylate
S Styrene
MMA Methyl methacrylate
AA Acrylic acid
MAA Methacrylic acid

Example 1

Bulk Synthesis of Gradient Copolymer

The mixture of reactants is as follows:

| | |
|---|---|
| MONAMS: 3.0 g | |
| SG1: 0.18 g | |
| Ethyl acrylate (EA): 480 g | i.e. 80% by weight/total weight of monomers |
| Styrene (S): 60 g | i.e. 10% by weight/total weight of monomers |
| Methacrylic acid (MAA): 60 g | i.e. 10% by weight/total weight of monomers |

All the constituents are mixed, in the absence of solvent, under a nitrogen atmosphere, and are then heated at a temperature maintained between 110 and 115° C. for 198 minutes.

Figure 2:
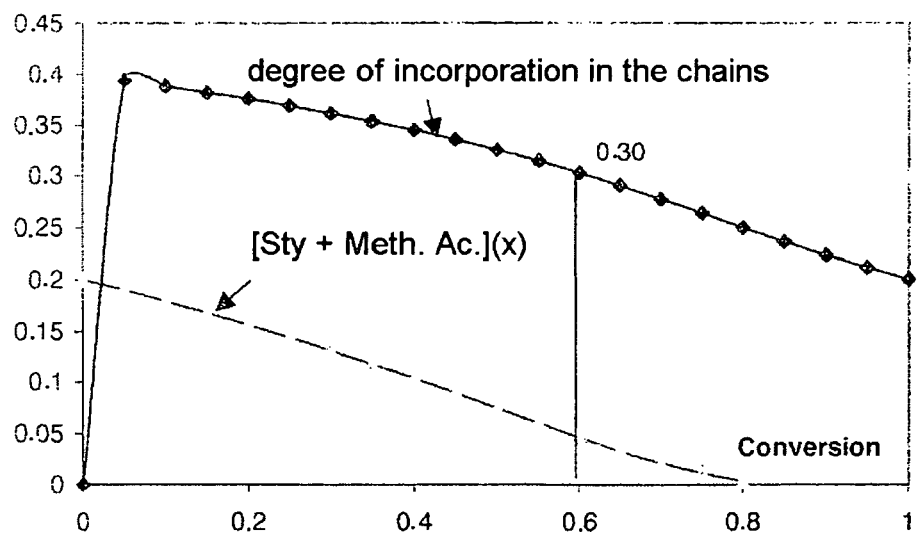
FIG. 2 is a plot representing a calculation of the incorporation of a styrene/methacrylic acid mixture as a function of the conversion.

The calculation of the gradient by simulation gives the curve in FIG. 2. The validity of this model is given by the monitoring of the relative concentrations of the three monomers by gas chromatography and NMR analysis of the polymers.

It is found that, at 60% conversion, the chemical composition of the copolymer is: 68.4% ethyl acrylate, 16.1% styrene and 15.5% methacrylic acid, according to NMR on the calculated curve (69%).

STY and MAA in the above figure respectively indicate Styrene and Methacrylic Acid. The final composition of the copolymer is as follows:
  ethyl acrylate: 68.4% by weight,
  styrene: 16.1% by weight,
  methacrylic acid: 15.5% by weight.

By LAC, the plot of the polymer shows a low polydispersity of the chemical composition of the chains.

The measurement of the masses by steric exclusion chromatography leads to the following results:

Mn=32 140 g/mol and Mw=51 700 g/mol, giving a polydispersity index PI=1.6.

A diagrammatic representation of the copolymer obtained may be as follows:

in which the dark spheres denote the styrene/methacrylic acid sequences and the white spheres denote the ethyl acrylate sequences.

Example 2

Bulk Synthesis of Gradient Copolymer

Different copolymers were prepared, according to the procedure described in example 1, from the following mixture of reactants:
  MONAMS: 3.0 g
  SG1: 0.18 g
  Styrene: 60 g
  Methacrylic acid: 60 g
  Acrylate (or mixture of acrylate): 480 g

| Example | Acrylate | Characteristics of the copolymer | Final composition of the copolymer (% by weight) |
|---|---|---|---|
| 2a | Butyl acrylate (BuA) | Mn = 31 100 g/mol<br>Mw = 52 930 g/mol<br>PI = 1.7 | Styrene: 18<br>Methacrylic acid: 22<br>Butyl acrylate: 60 |
| 2b | Methyl acrylate (MeA) | Mn = 32 750 g/mol<br>Mw = 61 470 g/mol<br>PI = 1.88 | Styrene: 20<br>Methacrylic acid: 21<br>Methyl acrylate: 59 |
| 2c | 50/50 by weight butyl acrylate/ ethyl acrylate (EA) mixture | Mn = 29 690 g/mol<br>Mw = 51 630 g/mol<br>PI = 1.74 | Styrene: 18<br>Methacrylic acid: 16<br>Acrylates: 66 |

Example 3

Synthesis in the Presence of Solvent

The same synthesis is carried out as in example 1 but in the presence of solvent. The mixture of reactants is as follows:
  MONAMS: 3.43 g
  SG1: 0.2 g
  Ethyl acrylate: 336 g
  Styrene: 42 g
  Methacrylic acid: 42 g
  Toluene: 180 g All the constituents are mixed, in toluene as solvent, under a nitrogen atmosphere, and are then heated at a temperature maintained between 110 and 115° C. for 198 minutes.

The final degree of conversion is 82% and the level of solid obtained is 57.2% by weight.

The analytical results below are determined:
Mn=30 570 g/mol, Mw=50 500 g/mol and PI=1.65.

The final composition of the copolymer is given by liquid absorption chromatography (LAC), which shows the similarity in composition with the copolymer prepared in example 1 and the absence of homopolymer in the materials. This is illustrated by curve 1 above given in example 1.

Example 4

Synthesis in the Presence of Solvent

The synthesis of a new copolymer is carried out according to the process of example 3 but in a different solvent: methyl ethyl ketone.

The starting composition of the mixture is:
  MONAMS: 4.893 g
  SG1: 0.2881 g
  Ethyl acrylate: 293.8 g
  Methyl acrylate: 32.66 g
  Styrene: 76.8 g Methacrylic acid: 76.8 g
Methyl ethyl ketone: 120 g The final degree of conversion is 99% and the level of solid obtained is 79.9%.

The analytical results below are determined:

Mn=30 500 g/mol

Mw=58 000 g/mol

PI=1.9

The incorporation of the monomers over time is measured by monitoring, by gas chromatography, the levels of residual monomers over time:

|  |  | Time | | | | | |
| --- | --- | --- | --- | --- | --- | --- | --- |
|  |  | 0 | 75 | 130 | 190 | 290 | 400 |
| Overall conversion |  | 0 | 16 | 30.5 | 49.5 | 85.4 | 99 |
| Residual monomers (%) | MeA | 5.45 | 5.1 | 3.75 | 3.75 | 1.6 | 0.13 |
|  | EA | 48.95 |  |  |  | 17.95 | 1.2 |
|  | MAA | 12.8 | 12.15 | 4.6 | 2 | 0.35 | 0.08 |
|  | S | 12.8 | 12.46 | 6.7 | 3.92 | 0.15 | 0.007 |

*The total level of residual monomers is calculated taking into account the solvent quantified by the level of solid.

It is noted that each monomer is present throughout the reaction.

The final composition of the copolymer is as follows:
- ethyl acrylate: 34% by weight
- methyl acrylate: 34% by weight
- styrene: 16% by weight
- methacrylic acid: 16% by weight

Example 5

An aqueous solution, with a level of solid of 10%, of the copolymer prepared in example 2a is prepared.

To do this, the polymer is dried beforehand in an oven. 10 g of polymer are then dissolved in 90 ml of water comprising 1.6 g of AMP (2-amino-2-methylpropanol). A clear and very fluid aqueous dispersion is obtained. The size of the particles, measured by scattering (Coulter 4NW device), is 33 nm.

Example 6

An aqueous solution of the copolymer prepared in example 1 is prepared. 10 g of polymer are dissolved in 40 g of tetrahydrofuran; 1.41 g of AMP (2-amino-2-methylpropanol), dissolved in 10 ml of water, are added. The solution thickens. 90 ml of demineralized water are then added slowly and with vigorous stirring. The solution remains clear and becomes fluid again.

The solvent is evaporated and a clear and fluid aqueous dispersion is obtained. The size of the particles, measured by scattering (Coulter 4NW device), is 199 nm.

Example 7

Example of the Use of a Gradient Copolymer Solution in the Manufacture of Solvent or Aqueous Gels 10 g of the copolymer of example 2b are diluted in 90 g of methyl ethyl ketone. 0.8 g of propyldiamine is added to the medium with stirring and a gel is instantaneously obtained.

10 g of the copolymer of example 7 are diluted in 90 ml of methyl ethyl ketone. 2 g of ethanol diisopropylamine are added to the medium. The medium remains fluid. 180 g of water are added to this solution. An aqueous gel is obtained.

What is claimed is:

1. A gradient copolymer comprising at least two different monomer units:
a) the first ($M_1$), the homopolymer of which has a $Tg_1$ of less than 20° C., representing at least 50% by weight of the total weight of the copolymer and selected from the group consisting of linear and branched $C_1$-$C_{12}$ alkyl acrylates, polyethylene glycol acrylate, polyethylene glycol methacrylate and dienes, b) the second ($M_2$), the homopolymer of which has a $T_{g2}$ of greater than 20° C., representing at most 50% by weight of the total weight of the copolymer and selected from the group consisting of styrene, styrene derivatives, acrylic acid, methacrylic acid, norbornyl acrylate, methyl methacrylate, acrylonitrile and methacrylonitrile, wherein at least 5% by weight of the total weight of the copolymer is represented by a hydrophilic monomer unit selected from the group consisting of polyethylene glycol acrylate, polyethylene glycol methacrylate, acrylic acid and methacrylic acid,
said gradient copolymer comprising at least one monomer $M_i$ such that the probability of encountering $M_i$ in any standardized position x situated on the polymer chain is nonzero; and wherein said gradient copolymer is soluble or dispersible in both water and in organic solvents at a concentration greater than or equal to 5%, and wherein said copolymer has number average and weight average masses of between 5,000 g/mol and 1,000,000 g/mol and a polydispersity index of between 1.1 and 2.5, said copolymer further comprising nitroxide residue unit.

2. The copolymer as claimed in claim 1, wherein $Tg_1$ is between −150 and 20° C.

3. The copolymer as claimed in claim 1, wherein the hydrophilic monomer represents at least 10% by weight of the total weight of the copolymer.

4. A process for producing the gradient copolymer of claim 1 comprising polymerizing by solution or bulk controlled radical polymerization, at a temperature of between 10 and 160° C., in the presence of a radical polymerization initiator and an agent for controlling the polymerization, a mixture of monomers comprising at least two monomers, the first ($M_1$), the homopolymer of which has a $Tg_1$ of less than 20° C., representing at least 50% by weight of the total weight of the mixture and selected from the group consisting of linear and branched $C_1$-$C_{12}$ alkyl acrylates, polyethylene glycol acrylate, polyethylene glycol methacrylate and dienes, the second ($M_2$), the homopolymer of which has a $T_{g2}$ of greater than 20° C., representing at most 50% by weight of the total weight of the mixture and selected from the group consisting of styrene, styrene derivatives, acrylic acid, methacrylic acid, norbornyl acrylate, methyl methacrylate, acrylonitrile and methacrylonitrile, wherein at least 5% by weight of the total weight of the mixture is a hydrophilic monomer selected from the group consisting of polyethylene glycol acrylate, polyethylene glycol methacrylate, acrylic acid and methacrylic acid, wherein the agent for controlling the polymerization is a nitroxide of general formula (I):

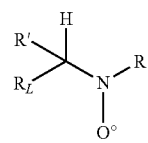

wherein R' and R, which are identical or different and which are optionally connected so as to form a ring, are alkyl groups having between 1 and 40 carbon atoms which are optionally substituted by hydroxyl, alkoxy or amino groups; and where $R_L$ is a monovalent group with a molar mass of greater than 16 g/mol which can be a phosphorus group or an aromatic group.

5. The process as claimed in claim 4, wherein the radical polymerization initiator and the agent for controlling the polymerization are replaced by a mixture composed of alkoxyamine corresponding to the following general formula (II) and of nitroxide corresponding to the general formula (I):

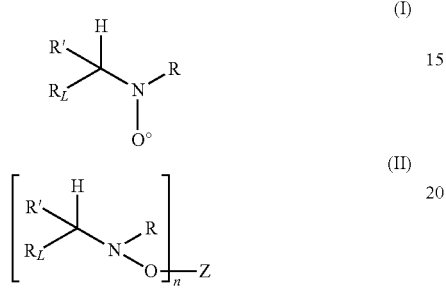

in which:
n is an integer of less than or equal to 8 and preferably of between 1 and 3,
Z is a carrying monovalent or polyvalent radical of styryl, acryloyl or methacryloyl type,
where R' and R, which are identical or different and which are optionally connected so as to form a ring, are alkyl groups having between 1 and 40 carbon atoms which are optionally substituted by hydroxyl, alkoxy or amino groups;
and where $R_L$ is a monovalent group with a molar mass of greater than 16 g/mol which can be a phosphorus group or an aromatic group, the nitroxide (I) representing at most 20% by weight of the total weight of the mixture.

6. The process as claimed in claim 4 wherein, $R_L$ is a phosphonate group of formula:

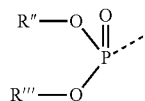

where R" and R''', which are identical or different and which are optionally connected so as to form a ring, are alkyl groups having between 1 and 40 carbon atoms which are optionally substituted by hydroxyl, alkoxy or amino groups.

7. A process for the aqueous dissolution, of the gradient copolymer of claim 1 comprising:
1) dissolving the copolymer in a ketone solution, at a level of solid of between 20 and 90%,
2) neutralizing the solution obtained in 1, if necessary, by addition of a molar solution either of acid or of base, the acid or base choice being conditioned by the chemical nature of the hydrophilic monomer, 3) adding water, with vigorous stirring, to the solution obtained in 1 or optionally in 2 in a proportion such that the level of solid obtained is between 1 and 80%; optionally, the water can be replaced by water/alcohol mixtures in proportions ranging from 99/1 to 50/50;
4) evaporating the ketone until the desired level of solid is obtained.

8. A paint, adhesive, glue or cosmetic formulation comprising the gradient copolymer of claim 1.

9. The copolymer of claim 1 wherein the homopolymer of the second monomer ($M_2$) has a $Tg_2$ of greater than 50° C.

10. The copolymer as claimed in claim 2, wherein $Tg_1$ is between −120 and 15° C.

11. The copolymer as claimed in claim 1, exhibiting a polydispersity index of between 1.1 and 2.

12. The process of claim 4 wherein said controlled radical polymerization occurs at a temperature of between 25 and 130° C.

13. The paint, adhesive, glue or cosmetic formulation of claim 8, wherein said formulation is an aqueous-based formulation.

14. The gradient copolymer of claim 1, wherein the first monomer unit $M_1$ is selected from the group consisting of methyl acrylate, ethyl acrylate, butyl acrylate or a mixture thereof and the second monomer unit $M_2$ is a mixture of styrene and methacrylic acid.

* * * * *